United States Patent
Al-Somali et al.

(10) Patent No.: US 12,215,075 B2
(45) Date of Patent: Feb. 4, 2025

(54) METHOD FOR THE PRODUCTION OF MTBE AND 1-BUTENE FROM A $C_4$ FEED STREAM

(71) Applicant: SABIC GLOBAL TECHNOLOGIES B.V., Bergen op Zoom (NL)

(72) Inventors: Mohammad Al-Somali, Jubail (SA); Ewa Gebauer-Henke, Geleen (NL); Aäron Vandeputte, Geleen (NL); Christian Okolo, Geleen (NL); Rasim Yagan, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/273,217

(22) PCT Filed: Sep. 3, 2019

(86) PCT No.: PCT/IB2019/057424
§ 371 (c)(1),
(2) Date: Mar. 3, 2021

(87) PCT Pub. No.: WO2020/049463
PCT Pub. Date: Mar. 12, 2020

(65) Prior Publication Data
US 2021/0347717 A1    Nov. 11, 2021

Related U.S. Application Data

(60) Provisional application No. 62/728,593, filed on Sep. 7, 2018.

(51) Int. Cl.
*C07C 41/06* (2006.01)
*C07C 5/25* (2006.01)
*C07C 7/04* (2006.01)
*C07C 41/42* (2006.01)

(52) U.S. Cl.
CPC ............ *C07C 41/06* (2013.01); *C07C 5/2506* (2013.01); *C07C 7/04* (2013.01); *C07C 41/42* (2013.01)

(58) Field of Classification Search
CPC .......... C07C 41/06; C07C 5/2506; C07C 7/04
See application file for complete search history.

(56) References Cited

U.S. PATENT DOCUMENTS

| | | |
|---|---|---|
| 4,513,153 A * | 4/1985 | Sandrin .................... C07C 11/08 585/315 |
| 4,558,168 A | 12/1985 | Gussow et al. |
| 4,797,133 A | 1/1989 | Pujado |
| 5,254,748 A | 10/1993 | Hensley et al. |
| 5,338,889 A | 8/1994 | Vora et al. |
| 5,352,848 A * | 10/1994 | Cottrell .................... C07C 41/34 585/800 |
| 5,382,707 A * | 1/1995 | Rubin ..................... C07C 41/06 568/697 |
| 5,563,299 A | 10/1996 | Paludetto et al. |
| 5,750,798 A | 5/1998 | Scharre et al. |
| 6,005,150 A | 12/1999 | Vora |
| 6,156,947 A | 12/2000 | Vora |
| 7,220,886 B2 | 5/2007 | Podrebarac et al. |
| 7,473,812 B2 | 1/2009 | Peters et al. |
| 7,485,761 B2 | 2/2009 | Schindler et al. |
| 7,737,318 B2 | 6/2010 | Santiago-Fernandez et al. |
| 7,932,428 B2 | 4/2011 | Rix et al. |
| 2006/0047176 A1 | 3/2006 | Gartside et al. |
| 2011/0034747 A1 * | 2/2011 | Gartside .................. C07C 4/04 585/326 |
| 2018/0029958 A1 * | 2/2018 | Keyvani ............... C07C 5/2213 |

FOREIGN PATENT DOCUMENTS

| | | | |
|---|---|---|---|
| CA | 2572510 A1 * | 6/2007 | ............. C07C 11/08 |
| FR | 2599377 | 12/1987 | |
| FR | 2812289 A1 * | 2/2002 | ............. C07C 41/06 |
| WO | WO 2008/133414 | 11/2008 | |
| WO | WO 2008/153643 | 12/2008 | |
| WO | WO 2015077338 | 5/2015 | |

OTHER PUBLICATIONS

International Search Report and Written Opinion issued in Corresponding PCT Application No. PCT/IB2019/057424, dated Oct. 29, 2019.
King, R.D. "Process Analysis in The Production of Methyl Tertiary Butyl Ether" *Technical Paper of ISA, Instrument Society of America* 1993, 48(part 1), 55-64.
Streich et al., "Secure the best benefits from C4 hydrocarbon processing—Part 1: Separation sequences" *Hydrocarbon Processing* 2016, 73-78.

* cited by examiner

*Primary Examiner* — Rosalynd A Keys
(74) *Attorney, Agent, or Firm* — NORTON ROSE FULBRIGHT US LLP

(57) ABSTRACT

Systems and methods for producing MTBE and 1-butene are disclosed. A crude C4 hydrocarbon stream is obtained by removing butadiene from a C4 hydrocarbon mixture of a hydrocarbon cracking unit. The crude C4 hydrocarbon stream is then distilled to form (a) a first distillate stream comprising isobutylene, isobutane, 1-butene, or combinations thereof and (b) a first bottom stream comprising 2-butene, n-butane, a deactivating compound for catalyst of MTBE synthesis. The first distillate stream is then flowed to a MTBE synthesis unit to produce via reaction with methanol. The raffinate from the MTBE synthesis unit comprising isobutane and 1-butene is further separated in a distillation column to produce 1-butene.

19 Claims, 3 Drawing Sheets

METHOD FOR THE PRODUCTION OF MTBE AND 1-BUTENE FROM A $C_4$ FEED STREAM

CROSS REFERENCE TO RELATED APPLICATIONS

This application is a national phase under 35 U.S.C. § 371 of International Application No. PCT/IB2019/057424, filed Sep. 3, 2019, which claims the benefit of priority to U.S. Provisional Patent Application Ser. No. 62/728,593, filed Sep. 7, 2018, the entire contents of each of which are hereby incorporated by reference in their entirety.

FIELD OF INVENTION

The present invention generally relates to systems and methods for producing methyl tert-butyl ether (MTBE) and 1-butene. More specifically, the present invention relates to integrated systems and methods for producing methyl tert-butyl ether (MTBE) and 1-butene that are capable of improving catalyst life for MTBE synthesis and increasing utilization rate of $C_4$ hydrocarbons from the feedstock compared to conventional MTBE production systems and methods.

BACKGROUND OF THE INVENTION

MTBE is used as a gasoline blending component. Typically, MTBE may be made by reacting isobutylene with methanol. The isobutylene for the reaction is usually obtained from a crude $C_4$ stream, which is usually a byproduct stream produced in a cracking process to produce olefins. More particularly, the crude $C_4$ stream can be obtained from steam cracking of hydrocarbons to produce ethylene and propylene. Generally, butadiene is removed from the crude $C_4$ stream before it is flowed into a MTBE synthesis unit.

The rest of the crude $C_4$ stream is then reacted with methanol in the MTBE synthesis unit in the presence of a catalyst to produce MTBE and a raffinate. The raffinate from the MTBE synthesis unit is further used to produce purified 1-butene. In this process, the raffinate is subsequently processed in a separation unit consisting of two rectifiers in series to produce purified 1-butene. However, generally, in the production process of MTBE and 1-butene, the catalyst life in the MTBE synthesis unit is relatively limited due to catalyst deactivating compounds mixed in the feedstock during the removal of butadiene. Furthermore, the hydrocarbons in this process are not fully utilized, resulting in waste of 2-butene and other $C_4$ hydrocarbons. Moreover, the 1-butene separating/purification step is relatively energy intensive, causing a high production cost for 1-butene.

Overall, while systems and methods for producing MTBE and 1-butene exist, the need for improvements in this field persists in light of at least the aforementioned drawbacks.

BRIEF SUMMARY OF THE INVENTION

A solution to at least some of the above-mentioned problems associated with the systems and methods for producing MTBE and 1-butene has been discovered. The solution resides in an integrated system for producing MTBE and 1-butene and methods of using the integrated system. Notably, a distillation unit is added to separate catalyst deactivating compounds, as well as 2-butene and n-butane, from the $C_4$ mixture that enters the MTBE synthesis unit. The removal of the catalyst deactivating compounds can improve the catalyst life for MTBE synthesis. The separated 2-butene can be further processed to produce propylene via metathesis or produce additional 1-butene via isomerization. Overall, the system and methods of the present invention can reduce the production cost for MTBE and/or 1-butene by increasing catalyst life expectancy and fully utilizing the $C_4$ feedstock. Therefore, the systems and the methods of the present invention provide a technical solution to at least some of the problems associated with the currently available methods for producing MTBE and 1-butene.

Embodiments of the invention include a method of producing methyl tertiary butyl ether (MTBE) and/or 1-butene. The method comprises distilling a crude $C_4$ hydrocarbon stream that comprises one or more of n-butane, 1-butene, 2-butene, isobutane, isobutene, 1,2-butadiene, 1,3-butadiene, and a catalyst deactivating compound comprising dimethylformamide (DMF), acetonitrile (ACN), n-methyl-2-pyrolidone (NMP), furfural methoxy-propio-nitrile (MOPN), or combinations thereof, to produce: (1) a distillate stream comprising isobutene, isobutane, and 1-butene; and (2) a bottom stream comprising 2-butene, n-butane, and the catalyst deactivating compound. The method further comprises reacting the isobutene (isobutylene) of the distillate stream with methanol in the presence of a catalyst for MTBE synthesis to produce methyl tertiary butyl ether and an unreacted portion of the distillate stream. The method further still comprises separating the methyl tertiary butyl ether from the unreacted portion of the distillate stream, the unreacted portion comprising isobutane and 1-butene.

Embodiments of the invention include a method of producing methyl tertiary butyl ether (MTBE) and/or 1-butene. The method comprises distilling a crude $C_4$ hydrocarbon stream that comprises one or more of n-butane, 1-butene, 2-butene, isobutane, isobutene, 1,2-butadiene, 1,3-butadiene, and a catalyst deactivating compound comprising dimethylformamide (DMF), acetonitrile (ACN), n-methyl-2-pyrolidone (NMP), furfural methoxy-propio-nitrile (MOPN), or combinations thereof, to produce: (1) a first distillate stream comprising one or more of isobutene, isobutane, and 1-butene; and (2) a first bottom stream comprising the catalyst deactivating compound and one or more of 2-butene and n-butane. The method further comprises reacting the isobutene of the distillate stream with methanol in the presence of a catalyst for MTBE synthesis to produce methyl tertiary butyl ether and an unreacted portion of the distillate stream. The method further comprises separating the methyl tertiary butyl ether from the unreacted portion of the distillate stream, the unreacted portion comprising isobutane and 1-butene. The method further still comprises distilling the unreacted portion to produce a second distillate stream comprising isobutane and a second bottoms stream comprising primarily 1-butene. The method further still comprises reacting the 2-butene of the first bottom stream with ethylene to produce propylene in an olefins conversion technology unit.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 1A shows a schematic diagram of a system for producing MTBE and 1-butene where the first bottom stream from the first distillation column is used as liquefied petroleum gas (LPG); FIG. 1B shows a schematic diagram of a system for producing MTBE and 1-butene where the first bottom stream from the first distillation column is flowed to an isomerization unit; FIG. 1C shows a schematic diagram of a system for producing MTBE and 1-butene where the first bottom stream from the first distillation column is flowed to an olefins conversion technology unit.

DETAILED DESCRIPTION OF THE INVENTION

Currently, MTBE is produced using a $C_4$ hydrocarbon mixture from a steam cracker as feedstock. The $C_4$ hydrocarbon mixture is first processed to remove butadiene and the isobutylene in the remainder of the $C_4$ hydrocarbon mixture is reacted with methanol to form MTBE and a raffinate. The raffinate from the MTBE synthesis unit is further distilled in two rectifiers in series to produce purified 1-butene. However, the catalyst deactivating compounds flowed into the MTBE synthesis unit with the remainder of the $C_4$ hydrocarbon mixture can significantly reduce the life expectancy for the catalyst of the MTBE synthesis unit. Furthermore, the $C_4$ hydrocarbon feedstock, especially 2-butene, is not fully utilized to minimize the production cost of MTBE and/or 1-butene. The present invention provides a solution to one or more of these problems. The solution is premised on a system and a method that include using a distillation column to separate the remainder of the $C_4$ hydrocarbon mixture that flows to the MTBE synthesis unit into a distillate stream that comprises 1-butene, isobutane and isobutylene, and a bottom stream that comprises 2-butene, n-butane and the catalyst deactivating compound. Thus, the catalyst deactivating compound is removed from the MTBE synthesis unit to avoid poisoning the catalyst for MTBE synthesis. Furthermore, the 1-butene can be separated from the raffinate from the MTBE synthesis unit with a single distillation step, rather than using two distillation steps in a conventional process resulting in reduced energy consumption for purifying 1-butene. Moreover, the separated 2-butene can be used to produce propylene via metathesis or be isomerized to produce additional 1-butene, thereby increasing the utilization rate of the $C_4$ hydrocarbon mixture and reducing the production costs for MTBE and/or 1-butene. These and other non-limiting aspects of the present invention are discussed in further detail in the following sections.

A. System for Producing MTBE and 1-Butene

Figure 1A:
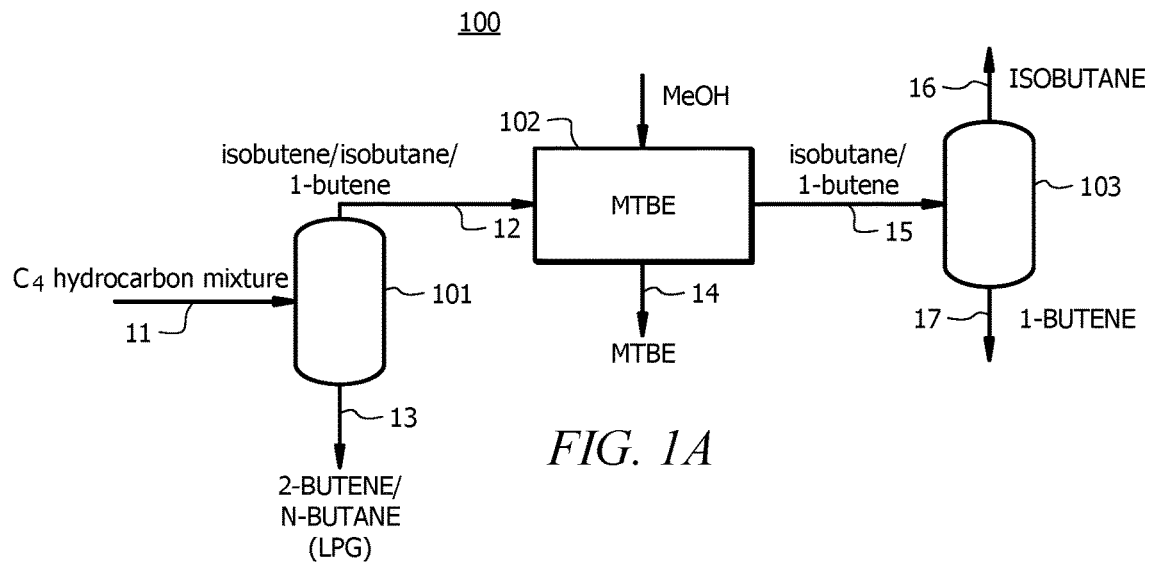
FIGS. 1A-1C show schematic diagrams of a system for producing MTBE and 1-butene, according to embodiments of the invention.
Figure 1B:
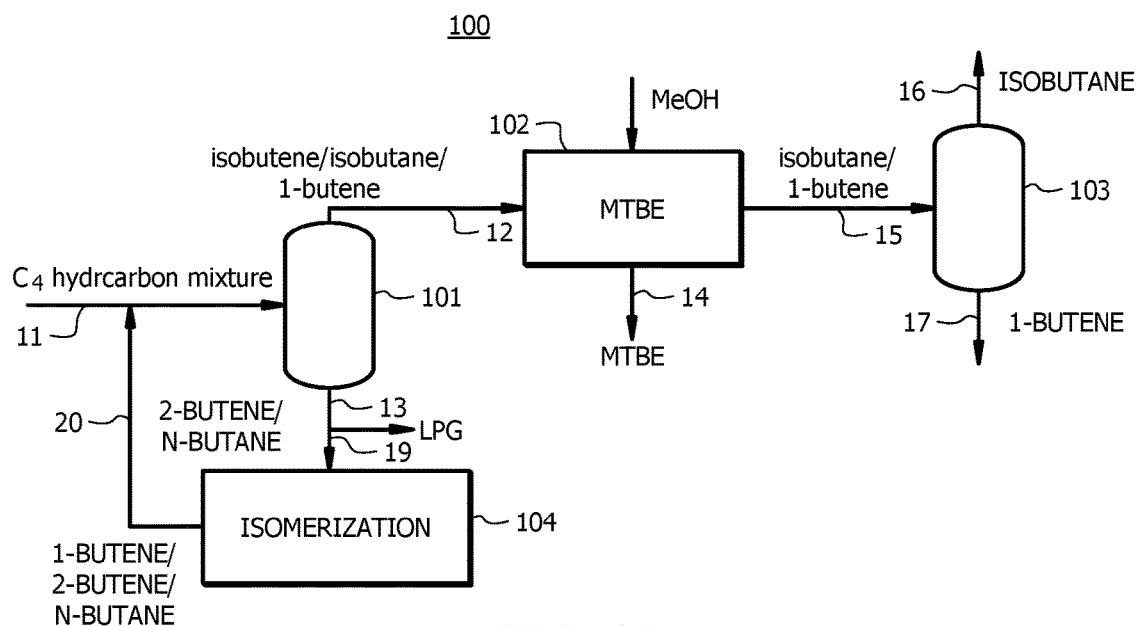
Figure 1C:
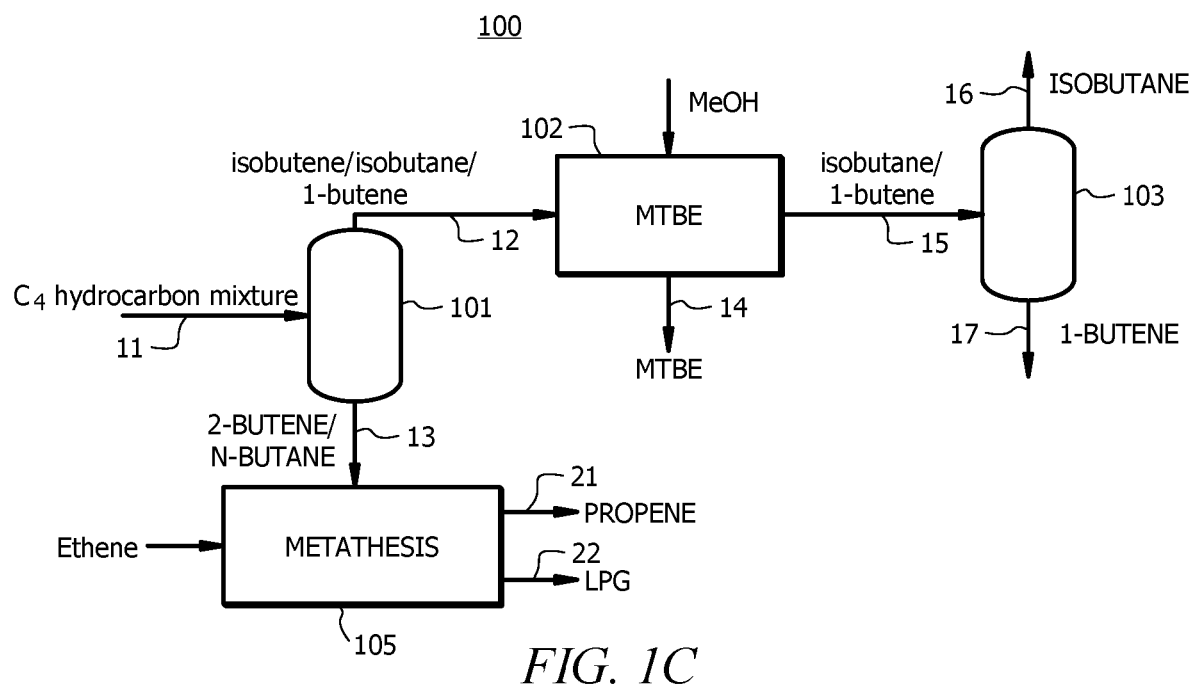

In embodiments of the invention, the system for producing MTBE and/or 1-butene can include a first distillation column, a MTBE synthesis unit, and a second distillation column. With reference to FIGS. 1A-1C, a schematic diagram is shown of system 100 for producing MTBE and/or 1-butene with an improved catalyst life expectancy and reduced production cost.

According to embodiments of the invention, system 100 may comprise first distillation column 101 configured to receive and distill crude $C_4$ hydrocarbon stream 11 to form: (1) first distillate stream 12 comprising isobutylene, isobutane, and 1-butene and (2) first bottom stream 13 comprising 2-butene and n-butane. In embodiments of the invention, crude $C_4$ hydrocarbon stream 11 may comprise 1-butene, 2-butene, isobutane, isobutylene, and n-butane. According to embodiments of the invention, crude $C_4$ hydrocarbon stream 11 may be obtained by flowing a $C_4$ hydrocarbon stream from a stream cracker and removing butadiene from the $C_4$ hydrocarbon stream to form $C_4$ hydrocarbon stream 11. According to embodiments of the invention, butadiene from the C$_4$ hydrocarbon stream may be removed via extraction and/or selective hydrogenation.

In embodiments of the invention, an overhead outlet of first distillation column 101 may be in fluid communication with MTBE synthesis unit 102 such that first distillate stream 11 flows from first distillation column 101 to MTBE synthesis unit 102. According to embodiments of the invention, MTBE synthesis unit 102 may include one or more MTBE synthesis reactors and one or more separation units. In embodiments of the invention, the one or more MTBE synthesis reactors may be configured to react isobutylene (isobutene) of first distillate stream 12 with methanol to produce MTBE. The one or more separation units may be configured to separate effluent from the one or more MTBE synthesis reactors to form (a) MTBE stream 14 comprising primarily MTBE and (b) raffinate stream 15 comprising primarily isobutane and 1-butene collectively. In embodiments of the invention, the MTBE synthesis reactor(s) may contain a catalyst selected from the group consisting of acidic resins, zeolites, fluorine promoted SiO$_2$—Al$_2$O$_3$ and sulfur promoted ZrO$_2$, or combinations thereof.

According to embodiments of the invention, an outlet of MTBE synthesis unit 102 may be in fluid communication with second distillation column 103 such that raffinate stream 15 flows from MTBE synthesis unit 102 to second distillation column 103. In embodiments of the invention, second distillation column 103 may be configured to separate raffinate stream 15 to form second distillate stream 16 comprising 50 to 99 wt. % isobutane, and 1-butene stream 17 comprising 95 to 99.9 wt. % 1-butene.

In embodiments of the invention, as shown in FIG. 1B, a bottom outlet of first distillation column 101 may be in fluid communication with isomerization unit 104 such that at least some of first bottom stream 13 flows from first distillation column 101 to isomerization unit 104. In embodiments of the invention, isomerization unit 104 may be configured to isomerize at least some 2-butene of first bottom stream 13 to 1-butene. Isomerization unit 104 may contain a catalyst including iridium pincer complex catalysts, or supported catalysts containing at least one noble metal from Group VIII, selected from the group consisting of ruthenium, rhodium, palladium, osmium, iridium and platinum, or nickel. The catalyst may be processed by a sulfur-containing compound, then by hydrogen prior to being used. According to embodiments of the invention, an outlet of isomerization unit 104 may be in fluid communication with an inlet of distillation column 101 such that isomerized recycle stream 20 from isomerization unit 104 flows from isomerization unit 104 to first distillation column 101. In embodiments of the invention, isomerized recycle stream 20 may be combined with crude C$_4$ hydrocarbon stream 11 before it flows to first distillation column 101. Isomerized recycle stream 20 may comprise one or more of 1-butene, 2-butene, and n-butane.

Alternatively or additionally, as shown in FIG. 1C, the bottom outlet of first distillation column 101 may be in fluid communication with olefins conversion technology unit 105 such that first bottom stream 13 flows from first distillation column 101 to olefins conversion technology unit 105. In embodiments of the invention, olefins conversion technology unit 105 may be configured to react at least some 2-butene of first bottom stream 13 with ethylene to produce propylene (propene) via metathesis. Olefins conversion technology unit may contain a catalyst comprising Schrock catalysts, tungsten oxide on silica or alumina support, molybdenum oxide on silica or alumina support, rhenium oxide on silica or alumina support, cobalt molybdate on alumina and mixtures therefor, or combinations thereof. In embodiments of the invention, olefins conversion technology unit 105 may comprise one or more metathesis reactors and one or more separation units such that a reaction stream from the one or more metathesis reactors is separated in the one or more separation units to form propylene stream 21 comprising primarily propylene (i.e., propene) and a LPG stream comprising n-butane and/or unreacted 2-butene.

B. Method of Producing MTBE and/or 1-Butene

Figure 2:
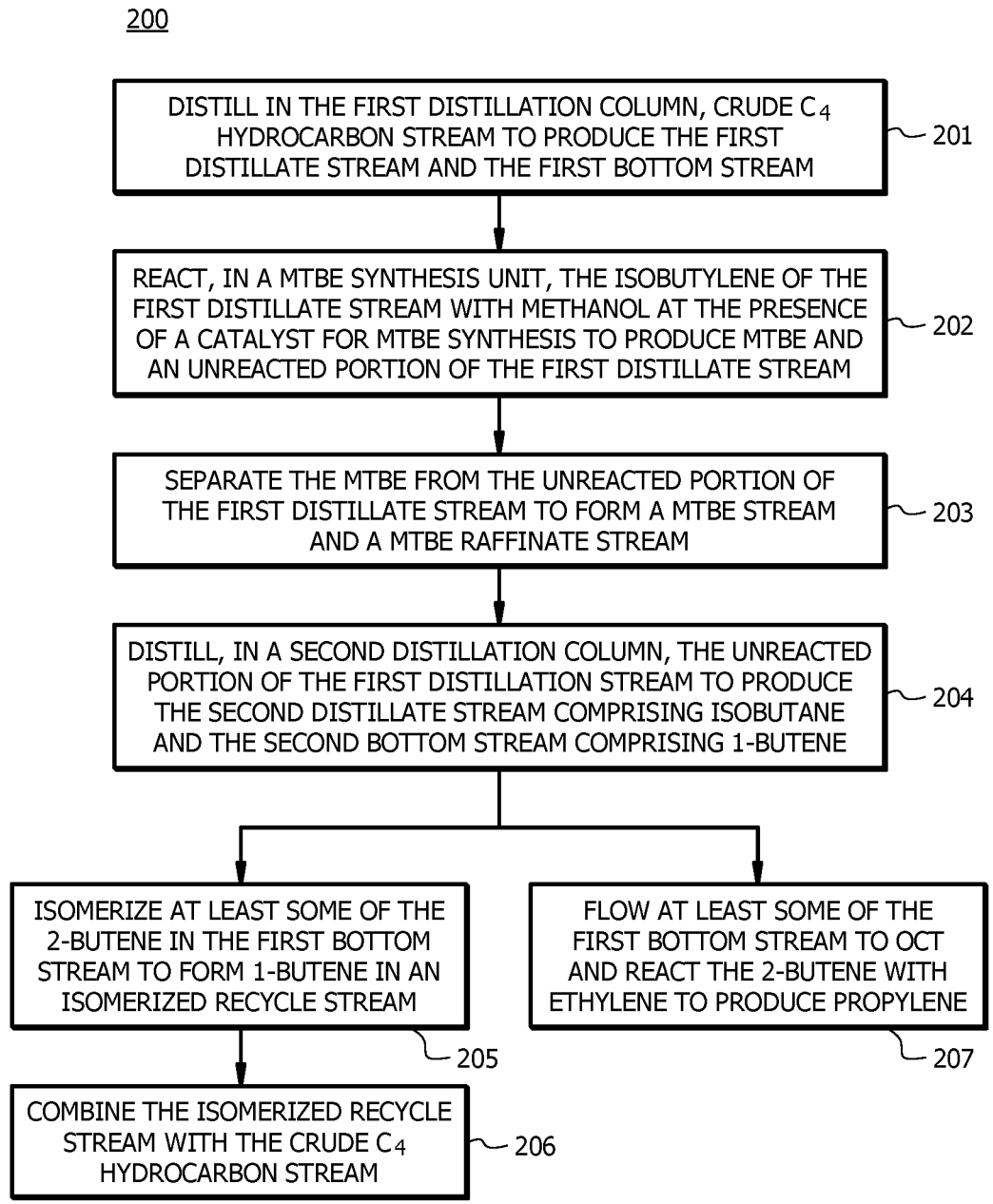
FIG. 2 shows a schematic flowchart for a method of producing MTBE and 1-butene, according to embodiments of the invention.

Methods of producing MTBE and/or 1-butene have been discovered for improving the life expectancy of the catalyst for MTBE synthesis, increasing the utilization rate of C$_4$ hydrocarbon feedstocks, and reducing the production costs for MTBE and 1-butene. As shown in FIG. 2, embodiments of the invention include method 200 for producing MTBE and/or 1-butene using crude C$_4$ hydrocarbon mixture as the feedstock. Method 200 may be implemented by system 100, as shown in FIGS. 1A to 1C. According to embodiments of the invention, method 200 may include distilling, in first distillation column 101, crude C$_4$ hydrocarbon stream 11 to produce first distillate stream 12 and first bottom stream 13, as shown in block 201.

In embodiments of the invention, crude C$_4$ hydrocarbon stream 11 may be obtained by removing butadiene from a C$_4$ hydrocarbon mixture from a steam cracker. According to embodiments of the invention, the C$_4$ hydrocarbon mixture from a steam cracker may comprise 1-butene, 2-butene, isobutylene, n-butane, butadiene, and isobutane. Removing butadiene from the C$_4$ hydrocarbon mixture from the steam cracker may be accomplished using solvent extraction. Crude C$_4$ hydrocarbon stream 11 may comprise n-butane, 1-butene, 2-butene, isobutane, isobutene, 1,2-butadiene, 1,3-butadiene, and a catalyst deactivating compound comprising dimethylformamide (DMF), acetonitrile (ACN), n-methyl-2-pyrolidone (NMP), furfural methoxy-propio-nitrile (MOPN), or combinations thereof. According to embodiments of the invention, crude C$_4$ hydrocarbon stream 11 may comprise 0 to 1 wt. % catalyst deactivating compound and all ranges and values there between including 0 to 0.1 wt. %, 0.1 to 0.2 wt. %, 0.2 to 0.3 wt. %, 0.3 to 0.4 wt. %, 0.4 to 0.5 wt. %, 0.5 to 0.6 wt. %, 0.6 to 0.7 wt. %, 0.7 to 0.8 wt. %, 0.8 to 0.9 wt. %, and 0.9 to 1.0 wt. %. In embodiments of the invention, the catalyst deactivating compound may be capable of deactivating a catalyst for MTBE synthesis. The catalyst deactivating compound may be introduced through the solvent extraction process for removing butadiene from the C$_4$ hydrocarbon mixture.

In embodiments of the invention, first distillate stream 12 may comprise primarily isobutylene, isobutane, and 1-butene, collectively. According to embodiments of the invention, first distillate stream 12 may further comprise 0 to 10 ppm catalyst deactivating compound and all ranges and values there between including 0 to 1 ppm, 1 to 2 ppm, 2 to 3 ppm, 3 to 4 ppm, 4 to 5 ppm, 5 to 6 ppm, 6 to 7 ppm, 7 to 8 ppm, 8 to 9 ppm, and 9 to 10 ppm. First bottom stream 13 may comprise primarily 2-butene, n-butane, and the catalyst deactivating compound. According to embodiments of the invention, first bottom stream 13 may include 0 to 10 wt. % catalyst deactivating compound and all ranges and values there between including ranges of 0 to 1 wt. %, 1 to 2 wt. %, 2 to 3 wt. %, 3 to 4 wt. %, 4 to 5 wt. %, 5 to 6 wt. %, 6 to 7 wt. %, 7 to 8 wt. %, 8 to 9 wt. %, and 9 to 10 wt. %. In embodiments of the invention, the catalyst deactivating compound may be flowed into first bottom stream 13, as shown in FIG. 1A, and then to a liquefied petroleum gas stream. In embodiments of the invention, distilling of crude C$_4$ hydrocarbon stream 11 in first distillation column 101 at block 201 may be carried out under operating conditions including a bottom boiling temperature range of 50 to 100° C. and all ranges and values there between including ranges of 50 to 55° C., 55 to 60° C., 60 to 65° C., 65 to 70° C., 70 to 75° C., 75 to 80° C., 80 to 85° C., 85 to 90° C., 90 to 95° C., and 95 to 100° C. The operating conditions of first distillation column 101 at block 201 may further include an overhead boiling temperature range of 30 to 60° C. and all ranges and values there between including ranges of 30 to 33° C., 33 to 36° C., 36 to 39° C., 39 to 42° C., 42 to 45° C., 45 to 48° C., 48 to 51° C., 51 to 54° C., 54 to 57° C., and 57 to 60° C. The operating conditions of first distillation column 101 at block 201 may further still include a molar reflux ratio in a range of 0.5 to 100 and all ranges and values there between including ranges of 0.5 to 1, 1 to 2, 2 to 3, 3 to 4, 4 to 5, 5 to 6, 6 to 7, 7 to 8, 8 to 9, 9 to 10, 10 to 20, 20 to 30, 30 to 40, 40 to 50, 50 to 60, 60 to 70, 70 to 80, 80 to 90, and 90 to 100. The operating conditions of first distillation column 101 at block 201 may further still include an operating pressure of 3 to 10 bar and all ranges and values there between including 4 bar, 5 bar, 6 bar, 7 bar, 8 bar, and 9 bar. In embodiments of the invention, a number of theoretical plates for first distillation column 101 may be in a range of 25 to 120 and all ranges and values there between including ranges of 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 105, 105 to 110, 110 to 115, and 115 to 120.

According to embodiments of the invention, method 200 may further include reacting, in MTBE synthesis unit 102, the isobutylene of first distillate stream 12 with methanol in the presence of a catalyst for MTBE synthesis to produce methyl tertiary butyl ether and an unreacted portion of first distillate stream 12, as shown in block 202. In embodiments of the invention, reacting in MTBE synthesis unit, at block 202 may be carried out at a reaction temperature of 30 to 120° C. and all ranges and values there between including ranges of 30 to 36° C., 36 to 42° C., 42 to 48° C., 48 to 54° C., 54 to 60° C., 60 to 66° C., 66 to 72° C., 72 to 78° C., 78 to 84° C., 84 to 90° C., 90 to 96° C., 96 to 102° C., 102 to 108° C., 108 to 114° C., and 114 to 120° C. Reacting in MTBE synthesis unit 102 at block 202 may be carried out at a reaction pressure of 5 to 20 bar and all ranges and values there between including ranges of 5 to 6 bar, 6 to 7 bar, 7 to 8 bar, 8 to 9 bar, 9 to 10 bar, 10 to 11 bar, 11 to 12 bar, 12 to 13 bar, 13 to 14 bar, 14 to 15 bar, 15 to 16 bar, 16 to 17 bar, 17 to 18 bar, 18 to 19 bar, and 19 to 20 bar. A volumetric ratio of methanol to first distillate stream 12 feeding to MTBE synthesis unit 102 may be in a range of 0 to 1 and all ranges and values there between including ranges of 0 to 0.1, 0.1 to 0.2, 0.2 to 0.3, 0.3 to 0.4, 0.4 to 0.5, 0.5 to 0.6, 0.6 to 0.7, 0.7 to 0.8, 0.8 to 0.9, and 0.9 to 1.0.

According to embodiments of the invention, as shown in block 203, method 200 may further include separating the MTBE from the unreacted portion of first distillate stream 12 to form MTBE stream 14 comprising primarily MTBE and raffinate stream 15 comprising primarily isobutane and 1-butene. In embodiments of the invention, at block 203, about 95 to 100% of MTBE that is produced at block 202 may be recovered. In embodiments of the invention, MTBE stream 14 may comprise 97 to 100 wt. % MTBE. Raffinate stream 15 may comprise about 5 to 95 wt. % 1-butene and about 5 to 95 wt. % isobutane. In embodiments of the invention, the separating at block 203 may be carried out in the separation unit of MTBE synthesis unit comprising one or more distillation columns, reactive distillation columns, or combinations thereof.

According to embodiments of the invention, as shown in block 204, method 200 may further include distilling, in second distillation column 103, raffinate stream 15 to produce second distillate stream 16 comprising 50 to 99 wt. % isobutane and second bottom stream 17 comprising 95 to 99.9 wt. % 1-butene. In embodiments of the invention, the distilling in second distillation column 103 at block 204 may be carried out under operating conditions comprising an overhead boiling temperature range of 30 to 60° C. and all ranges and values there between including ranges of 30 to 33° C., 33 to 36° C., 36 to 39° C., 39 to 42° C., 42 to 45° C., 45 to 48° C., 48 to 51° C., 51 to 54° C., 54 to 57° C., and 57 to 60° C. The bottom boiling temperature range of the distilling at block 204 may be 40 to 70° C. and all ranges and values there between including ranges of 40 to 43° C., 43 to 46° C., 46 to 49° C., 49 to 52° C., 52 to 55° C., 55 to 58° C., 58 to 61° C., 61 to 64° C., 64 to 67° C., and 67 to 70° C. The operation conditions of second distillation column 103 may further include a molar reflux ratio in a range of 1 to 100 and all ranges and values there between including ranges of 1 to 2, 2 to 3, 3 to 4, 4 to 5, 5 to 6, 6 to 7, 7 to 8, 8 to 9, 9 to 10, 10 to 20, 20 to 30, 30 to 40, 40 to 50, 50 to 60, 60 to 70, 70 to 80, 80 to 90, and 90 to 100. Second distillation column 103 may have a theoretical plates number in a range of 20 to 120 and all ranges and values there between including ranges of 20 to 30, 30 to 40, 40 to 50, 50 to 60, 60 to 70, 70 to 80, 80 to 90, 90 to 100, 100 to 110, and 110 to 120.

According to embodiments of the invention, method 200 may further include isomerizing, in isomerization unit 104, at least some of the 2-butene in first bottom stream 13 to form 1-butene in isomerized recycle stream 20, as shown in block 205. In embodiments of the invention, isomerized recycle stream 20 may comprise 1-butene, 2-butene, n-butane, or combinations thereof. Isomerized recycle stream 20 may further include the catalyst deactivating compounds. As an alternative to or in additional to flowing deactivating compounds in recycle stream 20, the catalyst deactivating compound from first bottom stream 13 may be removed by a guard bed (not shown in FIG. 1B) before first bottom stream 13 enters isomerization unit 104. As an alternative to or in addition to being removed, the catalyst deactivating compound may pass through isomerization unit 104. According to embodiments of the invention, isomerizing in isomerization unit 104 at block 205 may be carried out at a reaction temperature of 100 to 700° C. and a reaction pressure of 3 to 40 bar. In embodiments of the invention, at block 205, 2-butene may be converted at a conversion rate of 0 to 30% and all ranges and values there between including ranges of 0 to 3%, 3 to 6%, 6 to 9%, 9 to 12%, 12 to 15%, 15 to 18%, 18 to 21%, 21 to 24%, 24 to 27%, and 27 to 30%. In embodiments of the invention, method 200 may further still include combining isomerized recycle stream 20 with crude $C_4$ hydrocarbon stream 11, as shown in block 206. The combined stream may be flowed to first distillation column 101.

Alternatively or additionally, according to embodiments of the invention, at least some of first bottom stream 13 may be flowed to olefins conversion technology unit 105 and reacted with ethylene under reaction conditions sufficient to produce propylene via metathesis, as shown in block 207. In embodiments of the invention, an unreacted portion of first bottom stream 13 may be separated from propylene to form LPG stream 22 comprising primarily n-butane and/or unreacted 2-butene. In embodiments of the invention, at block 207, the reaction conditions may include a reaction temperature in a range of 100 to 500° C. and all ranges and values there between including ranges of 100 to 120° C., 120 to 140° C., 140 to 160° C., 160 to 180° C., 180 to 200° C., 200 to 220° C., 220 to 240° C., 240 to 260° C., 260 to 280° C., 280 to 300° C., 300 to 320° C., 320 to 340° C., 340 to 360° C., 360 to 380° C., 380 to 400° C., 400 to 420° C., 420 to 440° C., 440 to 460° C., 460 to 480° C., and 480 to 500° C. The reaction conditions at block 207 may further include a reaction pressure of 10 to 100 bar and all ranges and values there between including 10 to 20 bar, 20 to 30 bar, 30 to 40 bar, 40 to 50 bar, 50 to 60 bar, 60 to 70 bar, 70 to 80 bar, 80 to 90 bar, and 90 to 100 bar. In embodiments of the invention, at block 207, unreacted ethene and unreacted 2-butene from olefins conversion technology unit 105 may be recycled to an inlet of olefins conversion technology unit 105, and the 2-butene may be converted at a conversion rate of 20 to 80% per pass and all ranges and values there between including 20 to 24%, 24 to 28%, 28 to 32%, 32 to 36%, 36 to 40%, 40 to 44%, 44 to 48%, 48 to 52%, 52 to 56%, 56 to 60%, 60 to 64%, 64 to 68%, 68 to 72%, 72 to 76%, and 76 to 80%. According to embodiments of the invention, a total conversion rate for the 2-butene at block 207 may be in a range of 70 to 99% and all ranges and values there between including 70 to 73%, 73 to 76%, 76 to 79%, 79 to 82%, 82 to 85%, 85 to 88%, 88 to 91%, 91 to 94%, 94 to 97%, and 97 to 99%. In embodiments of the invention, the deactivating compounds may pass through olefins conversion technology unit 105. As an alternative to or in addition to passing the deactivating compounds through olefins conversion technology unit 105, the catalyst deactivating compound may be removed by a guard bed (not shown in FIG. 1C) before first bottom stream 13 enters olefins conversion technology unit 105. In embodiments of the invention, the catalyst deactivating compound that passes through olefins conversion technology unit 105 may be flowed in LPG stream 22.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, a specific example is included below. The example is for illustrative purposes only and are not intended to limit the invention. Those of ordinary skill in the art will readily recognize parameters that can be changed or modified to yield essentially the same results.

EXAMPLE

Simulation of System for Producing MTBE and/or 1-Butene

Compositions of a first distillate stream (corresponding to first distillate stream 12 of FIG. 1A) (Table 2) and a second distillate stream 16 (corresponding to second distillate stream 16 of FIG. 1A) (Table 3) have been simulated using AspenPlus v10.0 for the system as shown in FIG. 1A. The simulation included flowing about 28 ton/hr of a $C_4$ hydrocarbon stream (corresponding to $C_4$ hydrocarbon stream 11 in FIG. 1A) to the first distillation column (corresponding to first distillation column 101 in FIG. 1A). The composition of the crude $C_4$ hydrocarbon stream is shown in Table 1. The first distillate stream was flowed to a MTBE synthesis unit (corresponding to MTBE synthesis unit 102 in FIG. 1A), where the isobutene in the first distillate stream was reacted with 8.1 ton/hr of methanol in two reactors within the MTBE synthesis unit. In the simulation, 7 ton/hr of the second distillate stream, which is rich in isobutane, was recycled and mixed with the first distillate stream before entering the MTBE synthesis unit.

In the simulation, about 20.8 ton/hr of a MTBE stream (corresponding to MTBE stream 14 in FIG. 1A) was formed and further recovered by two distillation columns. The raffinate from the MTBE synthesis unit comprising primarily 1-butene and isobutane was flowed to a second distillation column (corresponding to second distillation column 103 in FIG. 1A) to produce a second bottom stream comprising more than 98 wt. % 1-butene. Purity of 1-butene can be improved by increasing the duties of the second distillation column or increasing the ratio of methanol to isobutene in MTBE synthesis unit.

TABLE 1

Composition of crude $C_4$ hydrocarbon stream flowed into the first distillation column

| Component | Composition (wt fraction) |
| --- | --- |
| N-butane | 0.11 |
| Isobutane | 0.02 |
| 1-butene | 0.26 |
| Trans-2-butene | 0.07 |
| Cis-2-butene | 0.05 |
| Isobutene | 0.48 |
| Dimethylformamide (deactivation component) | 0.01 |

TABLE 2

Composition of the first distillate stream from the first distillation column

| Component | Composition (wt fraction) |
| --- | --- |
| N-butane | 0.004 |
| Isobutane | 0.027 |
| 1-butene | 0.343 |
| Trans-2-butene | <1000 ppm |
| Cis-2-butene | <1000 ppm |
| Isobutene | 0.627 |
| Dimethylformamide (deactivation component) | <1 ppm |

TABLE 3

Composition of the second distillate stream from the second distillation column

| Component | Composition (wt fraction) |
| --- | --- |
| N-butane | 0.005 |
| Isobutane | 0.284 |
| 1-butene | 0.704 |
| Trans-2-butene | <1000 ppm |
| Cis-2-butene | <1000 ppm |
| Isobutene | 0.006 |

In the context of the present invention, at least the following 19 embodiments are described. Embodiment 1 is a method of producing methyl tertiary butyl ether (MTBE) and/or 1-butene. The method includes distilling a crude $C_4$ hydrocarbon stream that contains n-butane, 1-butene, 2-butene, isobutane, isobutene, 1,2-butadiene, 1,3-butadiene, and a catalyst deactivating compound containing dimethylformamide (DMF), acetonitrile (ACN), n-methyl-2-pyrolidone (NMP), furfural methoxy-propio-nitrile (MOPN), or combinations thereof, to produce: (1) a distillate stream containing isobutene, isobutane, and 1-butene; and (2) a bottom stream containing 2-butene, n-butane, and the catalyst deactivating compound. The method further includes reacting the isobutene of the distillate stream with methanol in the presence of a catalyst for MTBE synthesis to produce methyl tertiary butyl ether and an unreacted portion of the distillate stream, and separating the methyl tertiary butyl ether from the unreacted portion of the distillate stream, the unreacted portion containing isobutane and 1-butene. Embodiment 2 is the method of embodiment 1, further including isomerizing, in an isomerization unit, at least some of the 2-butene in the bottom stream to form an isomerized recycle stream containing 1-butene, non-isomerized 2-butene, and n-butane, and combining the isomerized recycle stream with the crude $C_4$ hydrocarbon stream for the distilling step. Embodiment 3 is the method of embodiment 2, wherein the isomerization unit includes a catalyst selected from the group consisting of iridium pincer complex catalysts, or supported catalysts containing at least one noble metal from Group VIII selected from the group consisting of ruthenium, rhodium, palladium, osmium, iridium and platinum, or nickel. The catalyst is processed by a sulfur-containing compound, then by hydrogen prior to being used. Embodiment 4 is the method of either of embodiments 2 or 3, wherein the isomerizing is carried out at a temperature of 100 to 700° C. Embodiment 5 is the method of any of embodiments 2 to 4, wherein the isomerizing is carried out at a pressure of 3 to 40 bar. Embodiment 6 is the method of embodiment 1, further including flowing the bottom stream to an olefins conversion technology unit, and reacting at least some of the 2-butene of the bottom stream with ethylene in the olefins conversion technology unit to form an effluent containing propylene and liquefied petroleum gas. Embodiment 7 is the method of embodiment 6, wherein the olefins conversion technology unit contains a catalyst selected from the group consisting of Schrock catalysts, tungsten oxide on silica or alumina support, molybdenum oxide on silica or alumina support, rhenium oxide on silica or alumina support, cobalt molybdate on alumina and mixtures therefor or combinations thereof. Embodiment 8 is the method of either of embodiments 6 or 7, wherein the olefins conversion technology unit is operated at a temperature of 100 to 500° C. Embodiment 9 is the method of any of embodiments 6 to 8, wherein the olefins conversion technology unit is operated at a pressure of 10 to 100 bar. Embodiment 10 is the method of any of embodiments 1 to 9, wherein the distilling of the crude $C_4$ hydrocarbon stream is carried out under operating conditions including a bottom boiling range of temperature of 50 to 100° C., an overhead boiling range of 30 to 60° C., a molar reflux ratio in a range of 0.5 to 100, and a number of theoretical plates in a range of 25 to 120. Embodiment 11 is the method of any of embodiments 1 to 10, wherein the distilling of the crude $C_4$ hydrocarbon stream is carried out at a pressure of 3 to 10 bar. Embodiment 12 is the method of any of embodiments 1 to 11, wherein the catalyst deactivating compound is capable of deactivating the catalyst for MTBE synthesis. Embodiment 13 is the method of embodiment 1, further including distilling the unreacted portion to produce a second distillate stream containing isobutane and a second bottom stream containing primarily 1-butene. Embodiment 14 is the method of embodiment 13, wherein the distilling of the unreacted portion is carried out under operating conditions including a bottom boiling range temperature of 40 to 70° C., an overhead boiling range of 30 to 60° C., a molar reflux ratio in a range of 1 to 100, and a number of theoretical plates in a range of 20 to 120. Embodiment 15 is the method of either of embodiments 13 or 14, wherein the distilling of the unreacted portion is carried out at a pressure of 3 to 10 bar. Embodiment 16 is the method of any of embodiments 13 to 15, wherein the second bottom stream contains 95 to 99.9 wt. % 1-butene. Embodiment 17 is the method of any of embodiments 1 to 16, wherein the crude $C_4$ hydrocarbon stream contains 0 to 1 wt. % catalyst deactivating compound. Embodiment 18 is the method of any of embodiments 1 to 17, wherein the distillate stream further contains 0 to 10 ppm of the catalyst deactivating compound. Embodiment 19 is the method of any of embodiments 1 to 18, wherein the MTBE is separated at a recovery rate of 95 to 100% in the separating step.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing methyl tertiary butyl ether (MTBE) and/or 1-butene, the method comprising:

distilling a crude $C_4$ hydrocarbon stream that comprises n-butane, 1-butene, 2-butene, isobutane and isobutene, one or more of 1,2-butadiene and 1,3-butadiene, and a catalyst deactivating compound capable of deactivating the catalyst for MTBE synthesis to produce: (1) a distillate stream comprising isobutene, isobutane, and 1-butene; and (2) a bottom stream comprising 2-butene, n-butane, and the catalyst deactivating compound;

reacting the isobutene of the distillate stream with methanol in the presence of a catalyst for MTBE synthesis to produce methyl tertiary butyl ether and an unreacted portion of the distillate stream;

separating the methyl tertiary butyl ether from the unreacted portion of the distillate stream, the unreacted portion comprising isobutane and 1-butene; and flowing the bottom stream to an olefins conversion technology unit, and reacting at least some of the 2-butene of the bottom stream with ethylene in the olefins conversion technology unit to form an effluent containing propylene and a liquified petroleum gas stream;

distilling the unreacted portion of the distillate stream to produce a second distillate stream comprising isobutane and a second bottom stream comprising primarily 1-butene;

wherein the catalyst deactivating compound is selected from the group consisting of dimethylformamide, n-methyl-2-pyrrolidone, acetonitrile, furfural, methoxy-propionitrile, or combinations thereof;

wherein the MTBE is separated at a recovery rate of 95 to 100 wt. % in the separating step; and wherein distilling the unreacted portion of the distillate stream is carried out under operating conditions including a bottom boiling range of 40 to 70° C., an overhead boiling range of 30 to 60° C., a molar reflux ratio in a range of 55 to 100, and a number of theoretical plates in a range of 85 to 120.

2. A method of producing methyl tertiary butyl ether (MTBE) and/or 1-butene, the method comprising:

distilling a crude $C_4$ hydrocarbon stream that comprises n-butane, 1-butene, 2-butene, isobutane, isobutene, one or more of 1,2-butadiene and 1,3-butadiene, and a catalyst deactivating compound capable of deactivating the catalyst for MTBE synthesis to produce: (1) a distillate stream comprising isobutene, isobutane, and 1-butene; and (2) a bottom stream comprising 2-butene, n-butane, and the catalyst deactivating compound;

reacting the isobutene of the distillate stream with methanol in the presence of a catalyst for MTBE synthesis to produce methyl tertiary butyl ether and an unreacted portion of the distillate stream;

separating the methyl tertiary butyl ether from the unreacted portion of the distillate stream, the unreacted portion comprising isobutane and 1-butene;

isomerizing, in an isomerization unit, at least some of the 2-butene in the bottom stream to form an isomerized recycle stream comprising 1-butene, non-isomerized 2-butene, and n-butane;

combining the isomerized recycle stream with the crude $C_4$ hydrocarbon stream for the distilling step; and distilling the unreacted portion of the distillate stream to produce a second distillate stream comprising isobutane and a second bottom stream comprising primarily 1-butene;

wherein the MTBE is separated at a recovery rate of 95 to 100 wt. % in the separating step; and wherein the isomerizing is carried out at a pressure of 15 to 40 bar and distilling the unreacted portion of the distillate stream is carried out under operating conditions including a bottom boiling range of 40 to 70° C., an overhead boiling range of 30 to 60° C., a molar reflux ratio in a range of 55 to 100, and a number of theoretical plates in a range of 85 to 120.

3. The method of claim 2, wherein the isomerization unit comprises a catalyst selected from the group consisting of iridium pincer complex catalysts, or supported catalysts containing at least one noble metal from Group VIII, selected from the group consisting of ruthenium, rhodium, palladium, osmium, iridium and platinum, or nickel, and the catalyst is processed by a sulfur-containing compound, then by hydrogen prior to being used.

4. The method of claim 2, wherein the catalyst deactivating compound is selected from the group consisting of dimethylformamide, acetonitrile n-methyl-2-pyrrolidone, furfural, methoxy-propionitrile, or combinations thereof.

5. The method of claim 2, wherein the isomerizing is carried out at a pressure of 20 to 40 bar.

6. A method of producing methyl tertiary butyl ether (MTBE) and/or 1-butene, the method comprising:

distilling a crude $C_4$ hydrocarbon stream that comprises one or more of n-butane, 1-butene, 2-butene, isobutane, isobutene, 1,2-butadiene, 1,3-butadiene, and a catalyst deactivating compound capable of deactivating the catalyst for MTBE synthesis to produce: (1) a distillate stream comprising isobutene, isobutane, and 1-butene; and (2) a bottom stream comprising 2-butene, n-butane, and the catalyst deactivating compound;

reacting the isobutene of the distillate stream with methanol in the presence of a catalyst for MTBE synthesis to produce methyl tertiary butyl ether and an unreacted portion of the distillate stream;

separating the methyl tertiary butyl ether from the unreacted portion of the distillate stream, the unreacted portion comprising isobutane and 1-butene; flowing the bottom stream to an olefins conversion technology unit;

reacting at least some of the 2-butene of the bottom stream with ethylene in the olefins conversion technology unit to form an effluent comprising propylene and liquefied petroleum gas;

distilling the unreacted portion of the distillate stream to produce a second distillate stream comprising isobutane and a second bottom stream comprising primarily 1-butene;

wherein the catalyst deactivating compound is selected from the group consisting of dimethylformamide, acetonitrile, n-methyl-2-pyrrolidone, furfural, methoxy-propionitrile, or combinations thereof;

wherein the MTBE is separated at a recovery rate of 95 to 100% in the separating step;

wherein the olefins conversion technology unit is operated at a temperature of 100 to 500° C.; and wherein distilling the unreacted portion of the distillate stream is carried out under operating conditions including a bottom boiling range of 40 to 70° C., an overhead boiling range of 30 to 60° C., a molar reflux ratio in a range of 55 to 100, and a number of theoretical plates in a range of 85 to 120.

7. The method of claim 6, wherein the olefins conversion technology unit contains a catalyst selected from the group consisting of Schrock catalysts, tungsten oxide on silica or alumina support, molybdenum oxide on silica or alumina support, rhenium oxide on silica or alumina support, cobalt molybdate on alumina, and combinations thereof.

8. The method of claim 4, wherein the catalyst deactivating compound comprises dimethylformamide, acetonitrile n-methyl-2-pyrrolidone, methoxy-propionitrile, or combinations thereof.

9. The method of claim 1, wherein the distilling of the crude $C_4$ hydrocarbon stream is carried out under operating conditions including a bottom boiling range of 50 to 100° C., an overhead boiling range of 30 to 60° C., a molar reflux ratio in a range of 0.5 to 100, and a number of theoretical plates in a range of 25 to 120.

10. The method of claim 1, wherein the distilling of the crude $C_4$ hydrocarbon stream is carried out at a pressure of 3 to 10 bar.

11. The method of claim 1, wherein distilling the unreacted portion is carried out under operating conditions including a bottom boiling range of 40 to 70° C., an overhead boiling range of 30 to 60° C., a molar reflux ratio in a range of 60 to 100, and a number of theoretical plates in a range of 90 to 120.

12. The method of claim 1, wherein distilling the unreacted portion is carried out at a pressure of 3 to 10 bar.

13. The method of claim 1, wherein the second bottom stream comprises 95 to 99.9 wt. % 1-butene.

14. The method of claim 1, wherein the crude $C_4$ hydrocarbon stream comprises 0 to 1 wt. % catalyst deactivating compound.

15. The method of claim 1, wherein the distillate stream further comprises 0.1 to 10 ppm of the catalyst deactivating compound.

16. The method of claim 1, wherein the catalyst deactivating compound is dimethylformamide (DMF).

17. The method of claim 1, wherein the catalyst deactivating compound is n-methyl-2-pyrrolidone (NMP).

18. The method of claim 1, wherein the catalyst deactivating compound is furfural.

19. The method of claim 1, wherein the catalyst deactivating compound is methoxy-propionitrile (MOPN).

* * * * *